United States Patent [19]

Tsukahara et al.

[11] Patent Number: 5,728,879
[45] Date of Patent: Mar. 17, 1998

[54] BISGUANIDINE SALTS AND A METHOD FOR RELEASING A BASE USING THE SAME SALTS

[75] Inventors: Jiro Tsukahara; Kiyoshi Takeuchi; Hideaki Satoh; Shun-ichi Ishikawa; Keizo Ogawa; Tomomi Ishino, all of Kanagawa, Japan

[73] Assignee: Fuji Photo Film Co., Ltd., Kanagawa, Japan

[21] Appl. No.: 829,814

[22] Filed: Mar. 25, 1997

Related U.S. Application Data

[63] Continuation of Ser. No. 527,532, Sep. 13, 1995, abandoned.

[30] Foreign Application Priority Data

Oct. 19, 1994 [JP] Japan .................................. 6-253637
Mar. 13, 1995 [JP] Japan .................................. 7-052774

[51] Int. Cl.$^6$ ...................... C07C 277/00; C07D 241/00
[52] U.S. Cl. ...................... 564/241; 430/203; 544/398; 548/312.7
[58] Field of Search .......................... 430/203; 564/241; 544/398; 548/312.7

[56] References Cited

U.S. PATENT DOCUMENTS 4,060,420  11/1977  Merkel et al. .......................... 96/114.1
4,981,965  1/1991  Yabuki et al. .......................... 548/312.7

FOREIGN PATENT DOCUMENTS 0308750  3/1989  European Pat. Off. .
0422662  4/1991  European Pat. Off. .
64-68746  3/1989  Japan .

OTHER PUBLICATIONS

Patent Abstracts of Japan, vol. 13, no. 215 (P–874) (3563) 19 May 1989 & JP–A–01 032 254 (Fuji Photo Film Co., Ltd.) 2 Feb. 1989.

*Primary Examiner*—Thorl Chea
*Attorney, Agent, or Firm*—Sughrue, Mion, Zinn, Macpeak & Seas, PLLC

[57] ABSTRACT

A bisguanidine salt selected from the group consisting of a 4-(phenylsulfonyl)phenylsulfonylacetic acid salt of N,N'-bis(1,3-diethylguanyl)ethylenediamine, a 4-(phenylsulfonyl)phenylsulfonylacetic acid salt of N,N'-bis(1,3-diisopropylguanyl)ethylenediamine, a 4-(phenylsulfonyl)phenylsulfonylacetic acid salt of N,N'-bis-(imidazoline-2-yl)ethylenediamine, a 4-(phenylsulfonyl)phenylsulfonylacetic acid salt of 1,4-bis(1,3-diisopropylguanyl)piperazine, a 4-(phenylsulfonyl)phenylsulfonylacetic acid salt of 1,4-bis(1,3-diethylguanyl)piperazine, a 4-(4-methylphenylsulfonyl)phenylsulfonylacetic acid salt of N,N'-bis(1,3-diethylguanyl)ethylenediamine and a 4-(4-ethylphenylsulfonyl)phenylsulfonylacetic acid salt of 1,4-bis(1,3-diethylguanyl)piperazine which can be used as a base precursor which is rapidly decomposed by heat treatment at 120° C. or less to release a base.

2 Claims, No Drawings

BISGUANIDINE SALTS AND A METHOD FOR RELEASING A BASE USING THE SAME SALTS

This is a Continuation of application Ser. No. 08/527,532 filed Sep. 13, 1995, now abandoned.

FIELD OF THE INVENTION

The present invention relates to bisguanidine salts useful as base precursors and a method for releasing a base using the same salts.

BACKGROUND OF THE INVENTION

Compounds from which bases are released by heating are referred to as "base precursors". The base precursors are employed in various systems designed so that the bases released by heating can function therein. Examples of such systems include heat-developable photographic materials, heat-sensitive recording materials, anion-polymerizable adhesives, film formation by coating, sealing materials, caulking materials, and the like.

One of the most favorable uses of the base precursors is for various types of image-forming materials for which heat is utilized (e.g., heat-developable photographic materials and heat-sensitive recording materials, etc.). In these materials the over all performance largely depends on the base precursor, because the formation of images takes place by reactions of other chemical species included therein which are activated by the base released by heating. The base precursor must rapidly release the base at a heating temperature as low as possible and be stable to store at the same time.

Examples of typical base precursors include salts of carboxylic acids and organic bases as described in U.S. Pat. No. 3,493,374 (triazine compounds and carboxylic acids), British Patent 998,949 (trichloroacetic acid salts), U.S. Pat. No. 4,060,420 (sulfonylacetic acid salts), JP-A-59-168441 (The term "JP-A" as used herein means an "unexamined published Japanese patent application") (sulfonylacetic acid salts), JP-A-59-180537 (propiolic acid salts), JP-A-60-237443 (phenylsulfonylacetic acid salts substituted by a sulfonyl group), and JP-A-61-51139 (sulfonylacetic acid salts). The use of these salts as the base precursors stems from the fact that decarboxylation of the carboxylic acids by heating results in the release of the organic bases. However, these precursors have been insufficient in compatibility of rapidity of the release of the bases on heat treatment (activity) with stability on storage (storability).

Base precursors consisting of carboxylic acids and organic di- to tetra-acidic bases are disclosed in JP-A-63-316760 and JP-A-1-68746 (corresponding to U.S. Pat. No. 4,981,965). In these base precursors, the activity on heat treatment at 140° C. is compatible with the storability. However, these specifications fail to provide base precursors which simultaneously satisfy both activity on heat treatment at 120° C. or less and storability.

Base precursors each has an inherent decomposition point. However, in practical applications rapid decomposition of the base precursors (the release of bases) is expected only at heating temperatures much higher than their decomposition points. Although ease of decomposition also is dependent on methods of heating, for example, in order to obtain rapid decomposition at a heating temperature of 120° C., the base precursors must usually have a decomposition point of about 100° C. or less. However, it has been quite difficult to find such base precursors, and even if they are found, they have had the disadvantage of poor storability. For that reason the base precursors which can function at heating temperatures of 120° C. or less have never been developed in spite of the expected usefulness thereof.

SUMMARY OF THE INVENTION

An object of the present invention is to provide base precursors which rapidly release a base at a low heating temperatures and have good storability at the same time.

The present inventors have synthesized and examined a wide scope of salts consisting of carboxylic acids having a decarboxylation property and organic bases, and as the result, found that the object of the present invention can be achieved by the use of the following extremely limited compounds, that is, a bisguanidine salt selected from the group consisting of a 4-(phenylsulfonyl) phenylsulfonylacetic acid salt of N,N'-bis(1,3-diethylguanyl)ethylenediamine, a 4-(phenylsulfonyl) phenylsulfonylacetic acid salt of N,N'-bis(1,3-diisopropylguanyl)ethylenediamine, a 4-(phenylsulfonyl) phenylsulfonylacetic acid salt of N,N'-bis-(imidazoline-2-yl)ethylenediamine, a 4-(phenylsulfonyl)-phenylsulfonylacetic acid salt of 1,4-bis(1,3-diisopropylguanyl)piperazine, a 4-(phenylsulfonyl) phenylsulfonylacetic acid salt of 1,4-bis(1,3-diethylguanyl) piperazine, a 4-(4-methylphenylsulfonyl) phenylsulfonylacetic acid salt of N,N'-bis(1,3-diethylguanyl)ethylenediamine and a 4-(4-ethylphenylsulfonyl)phenylsulfonylacetic acid salt of 1,4-bis(1,3-diethylguanyl)piperazine.

Further, another object of the present invention can be achieved by a method for releasing a base which comprises heating at least one of bisguanidine salts described above at 120° C. or less.

The structural formulae of the compounds described above are shown below.

Compound 1:

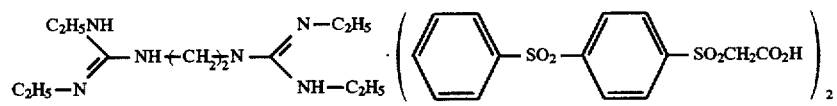

Compound 2:

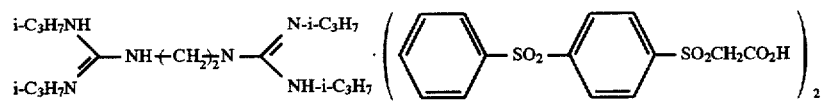

Compound 3:

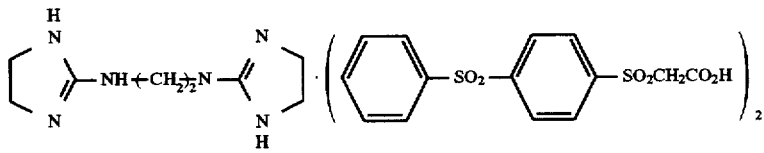

Compound 4:

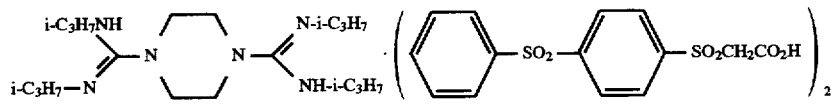

Compound 5:

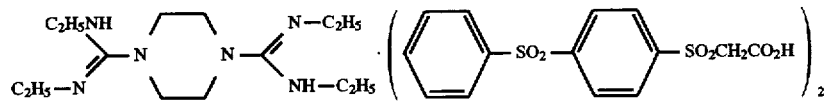

Compound 6:

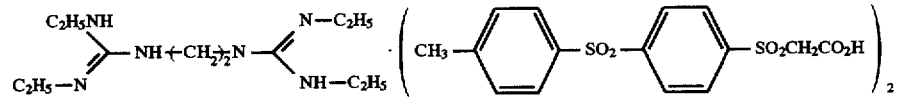

Compound 7:

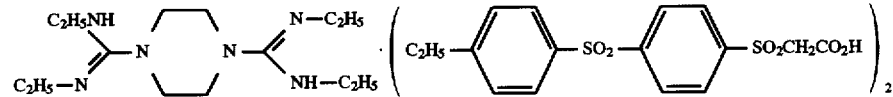

DETAILED DESCRIPTION OF THE INVENTION

The first feature of these compounds of the present invention is that the compounds have decomposition points of as low as about 100° C. Each base precursor has an inherent decomposition point. For example, a certain carboxylic acid salt has different decomposition points when the organic base moiety is different even if the carboxylic acid moiety is the same. There is no general tendency of base precursors similar in structure to have similar decomposition points, or a particular carboxylic acid salt or a particular organic base salt to always offer low decomposition points. It has been therefore impossible to search for base precursors based on an estimate of a decomposition point. The present inventors had to actually synthesize salts one by one to examine the decomposition points and base precursors having decomposition points of about 100° C. have been only rarely found. This fact is in detail explained hereinafter based on the data of decomposition points of a series of compounds which have been synthesized by the present inventor.

The second feature of the compounds of the present invention is stability on storage. In general, compounds having low decomposition points tend to show instability. It has been quite rare that compounds having decomposition points of about 100° C. offer stability on storage. Compounds which simultaneously satisfy both the activity and storability features are limited to the compounds of the present invention among compounds which the present inventors have synthesized and examined.

JP-A-1-68746 discloses 4-(phenylsulfonyl)-phenylsulfonylacetic acid and 4-(4-methylphenylsulfonyl)-phenylsulfonyl acetic acid as one of favorable carboxylic acids for base precursors, and N,N'-bis(1,3-diethylguanyl)-ethylenediamine and N,N'-bis(imidazolin-2-yl)-ethylenediamine as one of favorable organic bases as well. However, this specification fails to disclose the salts which are formed by combinations of these components, i.e., the above Compounds 1, 3 and 6 of the present invention.

As has been described above, the minimum unit for displaying the capability of a base precursor is neither a carboxylic acid nor an organic base, but a salt itself consisting of a carboxylic acid having decarboxylation property and an organic base. It cannot be easily expected from JP-A-1-68746 that the compounds of the present invention offer excellent capability because each base precursor has an unexpected, inherent decomposition point. The following examples show that the compounds of the present invention have much superior capability than compounds described in JP-A-1-68746 as base precursors and than compounds similar in structure to the compounds of the present invention.

EXAMPLES

Synthetic methods of the compounds of the present invention is described below. The compounds of this invention can be fundamentally obtained as sparingly soluble crystals by mixing one equivalent of bisguanidine and two equivalents of carboxylic acid in an alcoholic solvent. The resulting crystals are ordinary unhydrated salts, but sometimes hydrated salts.

The synthetic method is described in detail below.

Example 1 (Synthesis of Compound 1)

Synthesis of 4-(Phenylsulfonyl) phenylsulfonylacetic Acid:

A synthetic method of this compound is described in JP-A-60-113235 (page 8–9) in detail and also in the present invention the compound was synthesized according to this specification except that p-chlorodiphenylsulfone was used in place of p-bromodiphenylsulfone. Decomposition point: 194°–195° C. NMR (heavy methanol): δ8.2 (q, 4H), 8.0 (m, 2H), 7.6 (m, 3H), 4.4 (s, 2H).

Synthesis of N,N'-Bis(1,3-diethylguanyl) ethylenediamine:

In a vessel made of glass, 396.7 g (3.0 mol) of 1,3-diethylthiourea, 561 ml (3.3 mol) of 1-bromooctane and 1,000 ml of 2-propanol were mixed and refluxed with heating for 5 hr. To the reaction mixture 80.2 ml (1.2 mol) of ethylenediamine was added and refluxed with heating for 16 hr. The resulting reaction mixture was cooled to 10° C. to obtain N,N'-Bis(1,3-diethylguanyl)ethylenediamine hydrobromide as crystals. The crystals were filtered off, washed with ethyl acetate and then air-dried. Yield: 256 g. NMR (heavy dimethyl sulfoxide): δ7.5 (m, 6H), 3.4 (m, 4H), 3.2 (quintet, 8H), 1.1 (t, 12H).

In 1,400 ml of methanol, 200 g of the crystals was dissolved and 63 g of 85% potassium hydroxide was added to the solution and stirred for 1 hr at 25° C. Potassium bromide crystallized was filtered off and methanol was then removed by distillation to obtain 95 g of an intended oily product. NMR (heavy dimethyl sulfoxide): δ4.9 (broad s, 4H), 3.0 (s, 4H), 2.9 (q, 8H), 1.1 (t, 12H).

Synthesis of Compound 1:

A mixture of 34 g (0.1 mol) of 4-(phenylsulfonyl)-phenylsulfonylacetic acid and 680 ml of ethanol was heated to 70° C. to dissolve. The resulting solution was cooled to 40° C. and 12.8 g (0.05 mol) of N,N'-bis(1,3-diethylguanyl) ethylenediamine was then added thereto. The reaction mixture was cooled to 10° C. and a precipitate obtained was filtered off, washed with ethanol and then air-dried. The intended Compound 1 was obtained as crystals and the yield was 45 g.

The crystals was sufficiently dried and then measured with respect to a water content using the Karl Fischer's method. The water content measured was 3.8%. It is presumed that the crystals contain a water as a water of crystallization in an equimolecular amount to the carboxylic acid. NMR (heavy methanol): δ8.2 (q, 8H), 8.0 (m, 4H), 7.6 (m, 6H), 4.1 (s, 4H), 3.4 (s, 4H), 3.2 (q, 8H), 1.2 (t, 12H).

Example 2 (Synthesis of Compound 2)

Synthesis of N,N'-Bis(1,3-diisopropylguanyl)ethylenediamine:

To 126 g (1.0 mol) of 1,3-diisopropylcarbodiimide, 30 g (0.5 mol) of ethylenediamine was gradually added dropwise with stirring at 70° C. After finishing the addition, the temperature was raised to 90° C. and the reaction mixture was stirred for 1 hr. Thereafter, 200 ml of acetonitrile was added to the reaction mixture and cooled to room temperature. The crystals thus obtained was filtered off and washed with 200 ml of acetonitrile. Yield: 63 g. NMR (heavy water): δ3.7 (septet, 4H), 3.4 (s, 4H), 1.2 (d, 24H).

Synthesis of Compound 2:

Compound 2 was prepared in the same procedure as that for the synthesis of Compound 1 except that 15.6 g of N,N'-bis(1,3-diisopropylguanyl)ethylenediamine is used in place of 12.8 g of N,N'-bis(1,3-diethylguanyl)ethylenediamine. Compound 2 was obtained as crystals and the yield was 47.9 g. NMR (heavy methanol): δ8.2 (q, 8H), 8.0 (m, 4H), 7.6 (m, 6H), 4.1 (m, 4H), 3.8 (septet, 4H), 3.5 (s, 4H), 1.2 (d, 24H).

Example 3 (Synthesis of Compound 3)

Synthesis of N,N'-Bis(imidazolin-2-yl)ethylenediamine Hydrobromide:

In a vessel made of glass, 306 g (3.0 mol) of ethylenethiourea, 561 ml (3.3 mol) of 1-bromooctane and 1,000 ml of 2-propanol were mixed and refluxed with heating for 5 hr. To the reaction mixture, 80.2 ml (1.2 mol) of ethylenediamine was added and refluxed with heating for 16 hr. The resulting mixture was cooled to 10° C. and N,N'-bis (imidazolin-2-yl)ethylenediamine hydrobromide precipitated was filtered off, washed with 2-propanol and then air-dried. Yield: 223 g. NMR (heavy water): δ3.7 (s, 8H), 3.4 (s, 4H).

Synthesis of Compound 3:

In 1,400 ml of methanol, 200 g of N,N'-bis-(imidazolin-2-yl)ethylenediamine hydrobromide was dissolved and to the solution, 63 g of 85% potassium hydroxide was then added and stirred for 1 hr at 25° C. After potassium bromide precipitated was filtered out, methanol was removed by distillation to obtain N,N'-bis(imidazolin-2-yl) ethylenediamine as a solid. In 680 ml of ethanol, 34 g (0.1 mol) of 4-(phenylsulfonyl)phenylsulfonylacetic acid was heated to dissolve. To the cooled solution was then added 9.8 g (0.05 mol) of N,N'-bis(imidazolin-2-yl)ethylenediamine in ethanol and the resulting mixture was cooled to 10° C. A crystal precipitated was filtered off, washed and air-dried to obtain 42 g of the intended Compound 3 as crystals. NMR (heavy methanol): δ8.2 (q, 8H), 8.0 (m, 4H), 7.6 (m, 6H), 3.7 (s, 8H), 3.4 (s, 4H).

Example 4 (Synthesis of Compound 4)

Synthesis of 1,4-bis(1,3-diisopropylguanyl)piperazine:

A mixture of 43 g (0.5 mol) of piperazine and 126 g (1.0 mol) of 1,3-diisopropylcarbodiimide was heated with stirring to 70° C. The inner temperature rose to 90° C. by reaction heat. After the evolution of heat ceased, the reaction mixture was stirred at 90° C. for 2 hr. To the reaction mixture 200 ml of acetonitrile was added and the resultant mixture was cooled to room temperature to obtain intended crystals. The crystals were filtered off and washed with 200 ml of acetonitrile. Yield: 68 g. NMR (heavy water): δ3.7 (septet, 4H), 3.4 (s, 8H), 1.2 (d, 24H).

Synthesis of Compound 4:

Compound 4 was prepared in the same procedure as that for the synthesis of Compound 1 except that 16.9 g of N,N'-bis(1,3-diisopropylguanyl)piperazine was used in place of 12.8 g of N,N'-bis(1,3-diethylguanyl) ethylenediamine. Compound 4 was obtained as crystals and the yield was 45.1 g. NMR (heavy methanol): δ8.2 (q, 8H), 8.0 (m, 4H), 7.6 (m, 6H), 4.1 (m, 4H), 3.8 (septet, 4H), 3.5 (s, 4H), 1.3 (d, 24H).

Example 5 (Synthesis of Compound 4)

Synthesis of 1,4-bis(1,3-diethylguanyl)piperazine:

In 400 ml of tetrahydrofuran, 100.3 g (0.76 mol) of 1,3-diethylurea and 29.4 g (0.34 mol) of piperazine were dissolved, and to the solution, 850 g (3.8 mol) of lead monoxide was added and then refluxed with heating for 30 hours. The reaction mixture was cooled to a room temperature and then a metal salt was filtered off and removed. The filtrate was subjected to reduced pressure removal to obtain a yellow solid. The obtained yellow solid was recrystallized with acetonitrile to obtain 23.3 g (0.082 mol) of the intended 1,4-bis(1,3-diethylguanyl)piperazine being a white crystal. NMR (heavy dimethyl sulfoxide): δ4.9 (br, s, 2H), 3.0 (q, 8H), 2.9 (s, 8H), 1.0 (t, 12H).

Synthesis of Compound 5:

Compound 5 was prepared in the same procedure as that for the synthesis of Compound 1 except that 14.1 g of N,N'-bis(1,3-diethylguanyl)piperazine was used in place of 12.8 g of N,N'-bis(1,3-diethylguanyl)ethylenediamine. Compound 5 was obtained as crystals and the yield was 42.4 g. It is presumed that the obtained crystals have a water of crystallization in view of a water content of 5%. NMR (heavy methanol-heavy water-mixed solvent): δ8.3-8.1 (m, 8H), 8.0 (d, 2H), 7.8-7.7 (m, 6H), 4.2 (s, 4H), 3.5 (s, 8H), 1.3 (t, 12H).

Example 6 (Synthesis of Compound 6)

Synthesis of 4-methyl-4'-chlorodiphenylsulfone:

To 150 ml of chlorobenzene, 100.1 g (0.75 mol) of aluminum chloride was added, and further 143 g (0.75 mol) of p-toluenesulfonyl chloride was added dropwise over 1 hour. After stirred for 3 hours at 55° C., the reaction mixture was poured into 1.5 liter of water, and then the obtained crystal was filtered off and washed with n-hexane to obtain 140 g of the intended 4-methyl-4'-chlorodiphenylsulfone. NMR (heavy chloroform): δ7.9-7.8 (m, 4H), 7.5 (m, 2H), 7.3 (d, 2H), 2.4 (s, 3H).

Synthesis of 4-(4-methylphenylsulfonyl)phenylthio acetic acid:

In 250 ml of N,N-dimethylformamide, 140 g of 4-methyl-4'-chlorodiphenylsulfone was dissolved, and further 77 g of thioglycolic acid and 71 g of 85% potassium hydroxide pellet were added and stirred for 6 hours at 120° C. The reaction mixture was poured into 2-propanol and filtered off to obtain a precipitate. After the precipitate obtained was dissolved in water and then the insoluble matter was filtered off, 150 ml of concentrated chloric acid and 500 g of ice were added therein. The formed white crystal was filtered off and washed with water and further recrystallized with a mixed solvent of n-hexane and ethylacetate to obtain 110 g of the intended 4-(4-methylphenylsulfonyl)phenylthio acetic acid.

Synthesis of 4-(4-methylphenylsulfonyl)phenylsulfonylacetic acid:

To 100 g of 4-(4-methylphenylsulfonyl)phenylthio acetic acid, 50 ml of acetic acid and 1 g of sodium tungstate-dihydrate were added and then heated to 50° C. To the resulting solution, 77 g of 35% hydrogen peroxide solution was added dropwise over 2 hours, and then stirred for 1 hour at 60° C. The obtained reaction mixture was poured into water to obtain white crystals. The obtained white crystals were recrystallized with methanol to obtain 88 g of the intended 4-(4-methylphenylsulfonyl)phenylsulfonyl acetic acid. NMR (heavy methanol): δ8.3-8.1 (m, 4H), 7.5 (d, 2H), 7.5 (d, 2H), 4.7-4.6 (m, 2H), 2.4 (s, 3H).

Synthesis of Compound 6:

Compound 6 was prepared in the same manner as that for the synthesis of Compound 1 except that 35.4 g of 4-(4-methylphenylsulfonyl)phenylsulfonyl acetic acid was used in place of 34 g of 4-(phenylsulfonyl)phenylsulfonyl acetic acid. Compound 6 was obtained as crystals and the yield was 39.7 g. NMR (heavy methanol-heavy water-mixed solvent): δ8.2 (s, 8H), 7.9 (d, 4H), 7.4 (d, 4H), 4.1-4.0 (m, 4H), 3.5 (s, 4H), 3.3 (q, 8H), 2.4 (s, 6H), 1.2 (t, 12H).

Example 7 (Synthesis of Compound 7)

Synthesis of 4-ethyl-4'-chlorodiphenylsulfone:

The intended 4-ethyl-4'-chlorodiphenylsulfone was prepared in the same manner as in the synthesis of 4-methyl-4'-chlorodiphenylsulfone of Example 6 except that 153.5 g of 4-ethylbenzenesulfonyl chloride was used in place of 143 g of p-toluenesulfonyl chloride. The yield was 151.5 g. NMR (heavy chloroform): δ8.0-7.8 (m, 3H), 7.5 (d, 2H), 7.3 (d, 2H), 2.7 (q, 2H), 1.2 (t, 3H).

Synthesis of 4-(4-ethylphenylsulfonyl)phenylthio acetic acid:

The intended 4-(4-ethylphenylsulfonyl)phenylthio acetic acid was prepared in the same manner as in the synthesis of 4-(4-methylphenylsulfonyl)phenylthio acetic acid of Example 6 except that 151.5 g of 4-ethyl-4'-chlorodiphenylsulfone was used in place of 140 g of 4-methyl-4'-chlorodiphenylsulfone. The yield was 120.3 g. NMR (heavy dimethylsulfoxide): δ8.0-7.8 (m, 4H), 7.6-7.4 (m, 4H), 4.0 (s, 2H), 2.7 (q, 2H), 1.2 (t, 3H).

Synthesis of 4-(4-ethylphenylsulfonyl)phenylsulfonyl acetic acid:

The intended 4-(4-ethylphenylsulfonyl)phenylsulfonyl acetic acid was prepared in the same manner as in the synthesis of 4-(4-methylphenylsulfonyl)phenylsulfonyl acetic acid of Example 6 except that 104 g of 4-(4-ethylphenylsulfonyl)phenylthio acetic acid was used in place of 100 g of 4-(4-methylphenylsulfonyl)phenylthio acetic acid. The yield was 97.1 g. NMR (heavy methanol): δ8.3-8.1 (m, 4H), 7.9 (d, 2H), 7.4 (d, 2H), 4.4 (s, 2H), 2.7 (q, 2H), 1.2 (t, 3H).

Synthesis of Compound 7:

Compound 7 was prepared in the same manner as that for the synthesis of Compound 5 except that 39.3 g of 4-(4-ethylphenylsulfonyl)phenylsulfonyl acetic acid was used in place of 34 g of 4-(phenylsulfonyl)phenylsulfonyl acetic acid. The yield was 35 g. NMR (heavy methanol): δ8.3-8.1 (m, 8H), 7.9 (d, 2H), 7.4 (d, 2H), 4.1-4.0 (m, 4H), 3.5 (s, 8H), 3.2 (q, 2H), 2.7 (q, 2H), 1.4-1.1 (m, 18H).

Decomposition points of the compounds of the present invention and comparative compounds similar in structure thereto are shown in Table 1. The decomposition points were determined by visual observation using an ordinary melting-point apparatus. There were some comparative compounds of which decomposition points were not clearly observed on visual inspection. These decomposition points were replaced by temperatures giving endothermic peaks, when endothermic and gravimetric changes were simultaneously observed on heating at a temperature-increase rate of 10 K/min using an apparatus for conducting simultaneously both differential thermal analysis and thermogravimetry (manufactured by Seiko Instrument Inc.). Such decomposition points are given in parentheses in Table 1.

TABLE 1

Decomposition Point of Base Precursor

| Base Precursor | Decomposition Point (°C.) |
| --- | --- |
| Compound 1 (this invention) | 93–97 |
| Compound 2 (this invention) | 102–104 |
| Compound 3 (this invention) | 97–104 |
| Compound 4 (this invention) | 101–103 |
| Compound 5 (this invention) | 93–94 |
| Compound 6 (this invention) | 94–97 |
| Compound 7 (this invention) | 88–92 |
| Comparative Compound 1 | 128–135 |
| Comparative Compound 2 | 138–143 |

TABLE 1-continued

Decomposition Point of Base Precursor

| Base Precursor | Decomposition Point (°C.) |
|---|---|
| Comparative Compound 3 | 155–160 |
| Comparative Compound 4 | oily matter giving no distinct decomposition point |
| Comparative Compound 5 | 95–102 |
| Comparative Compound 6 | 118–124 |
| Comparative Compound 7 | 124–135 |
| Comparative Compound 8 | (121.0) |
| Comparative Compound 9 | 111–116 |
| Comparative Compound 10 | (99.7) |
| Comparative Compound 11 | 113–117 |
| Comparative Compound 12 | 122–127 |
| Comparative Compound 13 | (120.3) |
| Comparative Compound 14 | 116–122 |

Comparative Compound 1: (described as Compound 2 in JP-A-1-68746)

$$\begin{matrix} H_2N \\ \phantom{H_2}\diagdown \\ HN \end{matrix} \!\!-\!\! NH\!-\!(CH_2)_2\!-\!NH \!-\!\!\! \begin{matrix} \diagup NH \\ \phantom{\diagup} \\ \diagdown NH_2 \end{matrix} \cdot \left( \text{Ph}\!-\!SO_2\!-\!\text{Ph}\!-\!SO_2CH_2CO_2H \right)_2$$

Comparative Compound 2: (described as Compound 7 in JP-A-1-68746)

$$\begin{matrix} H_2N \\ \phantom{H_2}\diagdown \\ HN \end{matrix} \!\!-\!\! NH\!-\!(CH_2)_3\!-\!NH \!-\!\!\! \begin{matrix} \diagup NH \\ \phantom{\diagup} \\ \diagdown NH_2 \end{matrix} \cdot \left( \text{Ph}\!-\!SO_2\!-\!\text{Ph}\!-\!SO_2CH_2CO_2H \right)_2$$

Comparative Compound 3: (described as Compound 16 in JP-A-1-68746)

$$\begin{matrix} H_2N \\ \phantom{H_2}\diagdown \\ HN \end{matrix} \!\!-\!\! NH\!-\!(CH_2)_4\!-\!NH \!-\!\!\! \begin{matrix} \diagup NH \\ \phantom{\diagup} \\ \diagdown NH_2 \end{matrix} \cdot \left( \text{Ph}\!-\!SO_2\!-\!\text{Ph}\!-\!SO_2CH_2CO_2H \right)_2$$

Comparative Compound 4: (described as Compound 36 in JP-A-1-68746)

$$\begin{matrix} C_2H_5NH \\ \phantom{C_2H_5}\diagdown \\ C_2H_5\!-\!N \end{matrix} \!\!-\!\! NH\!-\!(CH_2)_2\!-\!NH \!-\!\!\! \begin{matrix} \diagup N\!-\!C_2H_5 \\ \phantom{\diagup} \\ \diagdown NH\!-\!C_2H_5 \end{matrix} \cdot \left( \text{Br}\!-\!\text{Ph}\!-\!SO_2CH_2CO_2H \right)_2$$

Comparative Compound 5: (described as Compound 40 in JP-A-1-68746)

$$\begin{matrix} H_2N \\ \phantom{H_2}\diagdown \\ HN \end{matrix} \!\!-\!\! NH\!-\!CH_2\!-\!\underset{\underset{CH_3}{|}}{CH}\!-\!NH \!-\!\!\! \begin{matrix} \diagup NH \\ \phantom{\diagup} \\ \diagdown NH_2 \end{matrix} \cdot \left( \text{Ph}\!-\!SO_2\!-\!\text{Ph}\!-\!SO_2CH_2CO_2H \right)_2$$

Comparative Compound 6:

$$\left( \underset{N}{\overset{\underset{H}{N}}{\diagup\diagdown}}\!-\!NH\!-\!(CH_2)_2\!-\!NH\!-\!\underset{\underset{H}{N}}{\overset{N}{\diagup\diagdown}} \right) \cdot \left( \text{Ph}\!-\!SO_2\!-\!\text{Ph}\!-\!SO_2CH_2CO_2H \right)_2$$

Comparative Compound 7:

$$\begin{matrix} CH_3NH \\ \phantom{CH_3}\diagdown \\ CH_3N \end{matrix} \!\!-\!\! NH\!-\!(CH_2)_2\!-\!NH \!-\!\!\! \begin{matrix} \diagup NCH_3 \\ \phantom{\diagup} \\ \diagdown NHCH_3 \end{matrix} \cdot \left( \text{Ph}\!-\!SO_2\!-\!\text{Ph}\!-\!SO_2CH_2CO_2H \right)_2$$

TABLE 1-continued

Decomposition Point of Base Precursor

| Base Precursor | Decomposition Point (°C.) |
|---|---|

Comparative Compound 8:

Comparative Compound 9:

Comparative Compound 10:

Comparative Compound 11:

Comparative Compound 12:

Comparative Compound 13:

Comparative Compound 14:

As described above, the compounds of this invention each has a decomposition point of about 100° C., whereas Comparative Compounds 1, 2, 3, 6, 7, 8, 9, 11, 12, 13 and 14 have decomposition points higher than 110° C. in spite of the similarity in structure to those of the compounds of the present invention.

It is clearly seen from the result of the example that the compounds of the present invention are superior to the comparative compounds as the base precursor.

Here, the relation between similarity of structure and decomposition point is explained below. The bisguanidine portion in Compounds 1 and 6 of the present invention is the same as that of Comparative Compound 14, but Compounds 1 and 6 are slightly different from Comparative Compound 14 in the terminal of the carboxylic acid portion. The difference of the decomposition point between Compounds 1 and 6 and Comparative Compound 14 is about 20° C.

In Compounds 6 and 7 of the present invention and Comparative Compounds 13 and 14, the carboxylic acid portion an the bisguanidine portion are exchanged each other.

Accordingly, the chemical structure of Compounds 6 and 7 and Comparative Compounds 13 and 14 are extremely similar. However, the difference of the decomposition point between the compound of the present invention and the comparative compound is 20° C. or more.

As is apparent from the result set forth in Table 1, there are many examples where the structure of compound is similar but the decomposition point is different.

Therefore, in the compounds of the present invention and the compounds similar to the compounds of the present invention, the decomposition point is varied by combination of the carboxylic acid portion and bisguanidine portion. That is, it is seen that the decomposition point cannot be expected from the partial structure of the carboxylic acid portion and bisguanidine portion.

Comparative Compound 4 (described as Compound 36 in JP-A-1-68746) is an oily substance which fails to give a distinct decomposition point, although it has a structure similar to that of Compound 1 of the present invention. Comparative Compound 5 (described as Compound 40 in JP-A-1-68746) has a structure similar to those of the compounds of the present invention and, in addition, has a decomposition point of about 100° C. Although comparative compound 10 has no structure similar to those of the compounds of the present invention, its decomposition point is about 100° C. Superiority of the compounds of this invention in storability over Comparative Compounds 4, 5 and 10 is proved in the following examples.

TEST EXAMPLE

The capability of the compounds of this invention as the base precursor is illustrated in detail by means of examples in which the bases are released from the compounds of the present invention.

Test Example 1

Solid Dispersion of Base Precursor:

A mixture of 75 g of a 4% aqueous solution of lime-processed gelatin, 5 g of an 5% aqueous solution of the following surfactant WW-1 and 20 g of Compound 1 of the present invention was dispersed in a grinding dispersion mixer containing 100 ml of glass beads having a diameter of 0.5 to 0.75 mm at 3,000 r.p.m. for 30 min. After removing the glass beads by filtration, the dispersion was adjusted to pH 6.5 with 1N sulfuric acid to obtain a 20% solid dispersion of the base precursor.

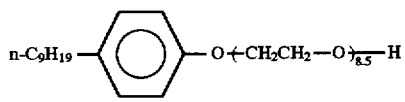

WW-1

Preparation of Base Precursor-Coated Sheet:

9.4 g of a 14% aqueous solution of lime-processed gelatin, 1.4 g of a dispersion containing both 8% of silica and 8% of gelatin, 7.3 g of a 20% dispersion of Compound 1, 31 g of water, 3.5 g of an 1% aqueous solution of the following surfactant WW-2, 1 g of 5% aqueous solution of surfactant WW-1, 11.8 g of 10% aqueous D-sorbitol, 2.5 g of a 5% aqueous solution of the following polymer P-1 for thickening, and 1.6 g of an 1.6% aqueous solution of the following hardener H-1 were mixed. A polyethylene terephthalate support having a thickness of 100 μm which was undercoated with gelatin was coated with the above solution in a wet coating amount of 48 ml/m² and dried to obtain a base precursor-coated sheet (Sample No. 1). The coating amount of the base precursor (Compound 1) was 1.0 g/m².

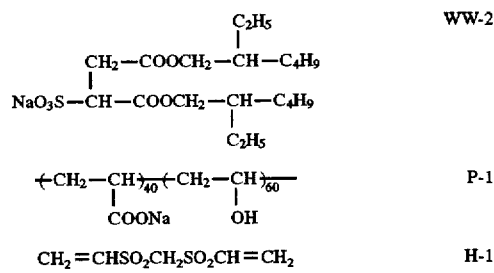

Evaluation of Activity for Base Precursor:

The support side of the base precursor-coated sheet (Sample No.1) was brought into contact with a heat block adjusted to a temperature of 120° C. and removed after 10 sec. After the sample was cooled to room temperature, the pH of the film and the proportion of decomposition of the base precursor were determined.

Evaluation of Storability for Base Precursor:

The base precursor-coated sheet (Sample No. 1) was allowed to stand for 72 hr in a vessel which was kept at an inner temperature of 45° C. and a relative humidity of 80%. The proportion of decomposition of the base precursor was then determined using a high performance liquid chromatography.

Test Example 2

Base precursor-coated sheets (Sample No. 2 to 21) were prepared and the activity and storability thereof were evaluated in the same manners as in Test Example 1, respectively, except that the compounds shown in Table 2 were used as base precursors in place of Compound 1 of the present invention.

TABLE 2

Preparation of Base Precursor-Sheet

| Sample No | Base Precursor | Coating Amount (g/m²) |
|---|---|---|
| 2 | Compound 2 (this invention) | 1.1 |
| 3 | Compound 3 (this invention) | 0.94 |
| 4 | Compound 4 (this invention) | 1.1 |
| 5 | Compound 5 (this invention) | 1.0 |
| 6 | Compound 6 (this invention) | 1.0 |
| 7 | Compound 7 (this invention) | 1.1 |
| 8 | Comparative Compound 1 | 0.88 |
| 9 | Comparative Compound 2 | 0.90 |
| 10 | Comparative Compound 3 | 0.91 |
| 11 | Comparative Compound 4 | 0.87 |
| 12 | Comparative Compound 5 | 0.90 |
| 13 | Comparative Compound 6 | 0.97 |
| 14 | Comparative Compound 7 | 0.95 |
| 15 | Comparative Compound 8 | 1.23 |
| 16 | Comparative Compound 9 | 0.92 |
| 17 | Comparative Compound 10 | 0.93 |
| 18 | Comparative Compound 11 | 1.1 |
| 19 | Comparative Compound 12 | 1.2 |
| 20 | Comparative Compound 13 | 1.1 |
| 21 | Comparative Compound 14 | 1.1 |

The results of Test Examples 1 and 2, as shown in Table 3 reflect that Compounds 1 to 7 of the present invention are rapidly decomposed under the heat condition of at 120° C. for 10 sec to release the corresponding bases, whereas the decomposition on storage at 45° is extremely depressed to prove good stability thereof. In Comparative Compounds 1, 2, 3, 6, 7, 8, 9, 11, 12, 13 and 14, the decomposition under the heating condition of at 120° C. is retarded, failing to fully raise the pH of the films. Although Comparative Compounds 4, 5 and 10 undergo relatively rapid decomposition at 120°

C., the decomposition on storage at 45° C. cannot be neglected and further the storability also is deteriorated.

TABLE 3

Capability of Base Precursor

| Sample No | Base Precursor | pH of Film | Activity (120° C., 10 sec) Proportion of Decomposition (%) | Storability (45° C.-80% RH, 72 hr) Proportion of Decomposition (%) |
|---|---|---|---|---|
| 1 | Compound 1 (this invention) | 11.2 | 69 | 4 |
| 2 | Compound 2 (this invention) | 10.8 | 40 | 2 |
| 3 | Compound 3 (this invention) | 10.4 | 31 | 5 |
| 4 | Compound 4 (this invention) | 11.4 | 80 | 2 |
| 5 | Compound 5 (this invention) | 11.4 | 76 | 5 |
| 6 | Compound 6 (this invention) | 11.1 | 65 | 7 |
| 7 | Compound 7 (this invention) | 11.8 | 92 | 16 |
| 8 | Comparative Compound 1 | 6.8 | 1 | >1 |
| 9 | Comparative Compound 2 | 7.1 | 4 | 1 |
| 10 | Comparative Compound 3 | 7.1 | 3 | >1 |
| 11 | Comparative Compound 4 | 10.6 | 40 | 92 |
| 12 | Comparative Compound 5 | 9.9 | 18 | 45 |
| 13 | Comparative Compound 6 | 8.0 | 6 | 3 |
| 14 | Comparative Compound 7 | 7.5 | 4 | 1 |
| 15 | Comparative Compound 9 | 7.6 | 4 | 3 |
| 16 | Comparative Compound 9 | 8.3 | 7 | 2 |
| 17 | Comparative Compound 10 | 9.3 | 13 | 36 |
| 18 | Comparative Compound 11 | 7.4 | 3 | 37 |
| 19 | Comparative Compound 12 | 7.2 | 4 | 10 |
| 20 | Comparative Compound 13 | 7.6 | 4 | 2 |
| 21 | Comparative Compound 14 | 7.3 | 3 | 5 |

The present invention can provide base precursors which are rapidly decomposed by heat treatment at a low temperature to release bases and have good storability.

While the invention has been described in detail and with reference to specific embodiments thereof, it will be apparent to one skilled in the art that various changes and modifications can be made therein without departing from the spirit and scope thereof.

What is claimed is:

1. A bisguanidine salt selected from the group consisting of a 4-(phenylsulfonyl)phenylsulfonylacetic acid salt of N,N'-bis(1,3-diethylguanyl)ethylenediamine, a 4-(phenylsulfonyl)phenylsulfonylacetic acid salt of N,N'-bis(1,3-diisopropylguanyl)ethylenediamine, a 4-(phenylsulfonyl)phenylsulfonylacetic acid salt of N,N'-bis-(imidazoline-2-yl)ethylenediamine, a 4-(phenylsulfonyl)-phenylsulfonylacetic acid salt of 1,4-bis(1,3-diisopropylguanyl)piperazine, a 4-(phenylsulfonyl)phenylsulfonylacetic acid salt of 1,4-bis(1,3-diethylguanyl)piperazine, a 4-(4-methylphenylsulfonyl)phenylsulfonylacetic acid salt of N,N'-bis(1,3-diethylguanyl)ethylenediamine and a 4-(4-ethylphenylsulfonyl)phenylsulfonylacetic acid salt of 1,4-bis(1,3-diethylguanyl)piperazine.

2. A bisguanidine salt selected from the group consisting of a 4-(phenylsulfonyl)phenylsulfonylacetic acid salt of N,N'-bis(1,3-diethylguanyl)ethylenediamine, a 4-(phenylsulfonyl)phenylsulfonylacetic acid salt of N,N'-bis(1,3-diisopropylguanyl)ethylenediamine, a 4-(phenylsulfonyl)phenylsulfonylacetic acid salt of N,N'-bis-(imidazoline-2-yl)ethylenediamine, a 4-(phenylsulfonyl)-phenylsulfonylacetic acid salt of 1,4-bis(1,3-diisopropylguanyl)piperazine, a 4-(phenylsulfonyl)phenylsulfonylacetic acid salt of 1,4-bis(1,3-diethylguanyl)piperazine, a 4-(4-methylphenylsulfonyl)phenylsulfonylacetic acid salt of N,N'-bis(1,3-diethylguanyl)ethylenediamine and a 4-(4-ethylphenylsulfonyl)phenylsulfonylacetic acid salt of 1,4-bis(1,3-diethylguanyl)piperazine, for a heat-developable photographic material and a heat-sensitive recording material.

* * * * *